United States Patent [19]

Morelli et al.

[11] 3,947,510

[45] Mar. 30, 1976

[54] HYDROGENATION OF LINEAR HYDROCARBON DIOLEFINS TO LINEAR HYDROCARBON OLEFINS

[75] Inventors: Morello Morelli, San Donato Milanese; Fortunato De Marco, Milan, both of Italy

[73] Assignee: Snamprogetti S.p.A., San Donato Milanese, Italy

[22] Filed: Dec. 30, 1974

[21] Appl. No.: 537,378

Related U.S. Application Data

[62] Division of Ser. No. 382,055, July 24, 1973, Pat. No. 3,857,894.

[52] U.S. Cl. .......... 260/677 H; 208/255; 260/683.9
[51] Int. Cl.² .................. C07C 11/00; C10G 17/00
[58] Field of Search ......... 260/677 R, 677 H, 683.9; 208/255

[56] References Cited

UNITED STATES PATENTS

| | | | |
|---|---|---|---|
| 3,715,404 | 2/1973 | Lindlar | 260/677 H |
| 3,821,323 | 6/1974 | Schulze et al. | 260/677 H |
| 3,857,894 | 12/1974 | Morelli et al. | 260/666 A |

*Primary Examiner*—Delbert E. Gantz
*Attorney, Agent, or Firm*—Ralph M. Watson

[57] ABSTRACT

A process is described whereby a linear hydrocarbon diolefin is selectively hydrogenated to a linear hydrocarbon olefin in the presence of a palladium base catalyst by adding to the reaction mixture an aqueous solution of a zinc salt such as zinc acetate wherein the ratio of water/zinc is at least 1/1 by weight.

6 Claims, No Drawings

HYDROGENATION OF LINEAR HYDROCARBON DIOLEFINS TO LINEAR HYDROCARBON OLEFINS

This is a division, of application Ser. No. 382,055, filed July 24, 1973, now U.S. Pat. No. 3,857,894.

The present invention relates to a process for the selective hydrogenation of diolefin hydrocarbons to olefin hydrocarbons.

It is already known that it is possible to hydrogenate diolefin compounds in the presence of palladium catalysts: however in the past a mixture of olefin and saturated compound was obtained with an uncontrolled selectivity in olefin compounds.

To reach satisfactory results and to stop the subsequent hydrogenation of the olefin compound to saturated compound, it has been proposed to partially deactivate the palladium catalyst, by impregnation or coprecipitation with salts of Pb, Zn, Hg, Cd, Th, Sn etc.

However said impregnation or coprecipitation methods are difficult to be practically carried out, in that the deactivation conditions of the catalyst (temperature, deactivating salt concentration, operating time) are very critical; as a matter of fact, by operating under conditions even slightly different from the optimum ones, catalysts are obtained wich are either non selective or wholly deactivated.

It is also known that to obtain a high selectivity catalyst it is necesary that the impregnation or coprecipitation treatment be carried out at a rather high temperature (80° to 100°C), which is, on the other hand, particularly disadvantageous in the case of supported catalysts.

We have now found that it is possible to obtain selectivity as close as to 100% in the hydrogenation of diolefin compounds to olefin compounds, by operating at relatively low temperature or in any case at a temperature ranging from 20°C to 60°C, by employing conventional palladium catalysts, possibly supported for instance on calcium carbonate or barium sulfate and by adding to the reaction mixture an aqueous solution of zinc salt. Therefore by operating according to the present invention it is possible to obtain selectivities as high as 100% without it being necessary to subject the palladium catalyst to the hot impregnating or coprecipitating operations which are very expensive and complicated the zinc is added continuously as an aqueous solution to the hydrogenation mixture. Beside the above practical and economical advantages, the present invention represents a further advance in that the life of the catalyst employed according to the invention, at the same selectivity values, is longer than the life of the known deactivated catalysts.

According to the present invention the passage of material to be hydrogenated and zinc salt on the catalyst in the course of the continuous tests can be effected for many times while obtaining always very good selectivity. The anion of the zinc salt has no importance as to the selectivity, but it is preferable that the salt have a high solubility in water. In this connection the chloride, sulfate, nitrate, acetate and oxalate are quite suitable.

The amount of salt can vary from 0.01 to 5% and preferably from 0.01 to 2% by weight with respect to the diolefin compound.

The minimum amount of water necessary for the good course of the reaction is such as to be sufficient to dissolve the zinc salt under the reaction conditions.

It is therefore necessary that there be a ratio water/zinc salt of at least 1/1 by weight.

On the other hand it is advisable to utilize a water/zinc salt ratio not higher than 50/1 in order to have a satisfactory reaction rate.

In the absence of water the hydrogenation of the diolefin compounds is not stopped at the 1st stage, i.e., at the formation of olefine compounds, but it goes on up to the production of saturated compounds.

It is preferable to add to the reaction mixture an amine compound, generally ammonia, in very low amounts, preferably lower than 0.5% by weight with respect to the diolefin compound, even though higher amounts, up to 20–30% do not negatively effect the reaction.

The present invention can be applied to continuous or discontinuous processes in a wide range of temperature, for instance between 20°C and 60°C, and of pressure, for instance from 1 to 50 atmospheres.

It is to be noted that the amount of the salt, which is to be added to the reaction mixture, depends, within the abovementioned ranges, the reaction rate, i.e. on the hydrogen pressure and the temperature, and also on the efficacy of stirring.

By operating according to the present invention, the absorption of hydrogen from the reaction mixture stops after one of the double bonds has been hydrogenated to a simple bond, then, by letting the reacted mixture at the reaction conditions also for relatively long times, a further hydrogenation does not substantially occur.

The present invention will be better illustrated by the following operative examples.

EXAMPLE 1

Cyclopentadiene was hydrogenated in the presence of 2% by weight of a Pd base catalyst on $CaCO_3$ as catalyst carrier (5% Pd) at the temperature of 30°C. 0.2% of ammonia, 0.2% of dehydrated zinc acetate and 0.4% by weight of water were added into an autoclave kept under stirring by means of a stirrer consisting of a hallow shaft for letting hydrogen be ricirculated. The hydrogen pressure was 5 $kg/cm^2$.

The course of the reaction was controlled by gas-chromatography anaylsis performed on samples drawn at regular intervals.

After 90' hydrogen absorption was no more noted and the selectivity as cyclopentene cyclopentene/cyclopentene + cyclopentane = % by moles was 99.4. Starting cyclopentadiene was practically absent. After another 90 minutes under the reaction conditions the selectivity was higher than 99%.

EXAMPLE 2

We operated according to example 1 but the water amount was 1%. After the disappearance of starting cyclopentadiene, the selectivity as cyclopentene of the obtained product was 99.2% and was practically constant also after a long time during which the product remained at the reaction conditions.

EXAMPLE 3

We operated according to example 1 but no water was added.

The selectivity as cyclopentene, after the dicyclopentadiene disappearance, was 89%; by keeping the product under the reaction conditions for 30 minutes again, the selectivity decreased up to 74% because of the formation of cyclopentane and, after 30 minutes again, the selectivity decreased to 60%.

EXAMPLE 4 AND 5

Isoprene and pentadiene were subjected to hydrogenation according to example 1.

After the total disappearance of the diolefins, mixtures were obtained of olefin isomers at selectivities respectively of 99.1 and 98.7.

What we claim is:

1. A process of hydrogenating a linear hydrocarbon diolefin by contacting said linear hydrocarbon diolefin with hydrogen in the presence of a palladium base catalyst, wherein the improvement comprises increasing the selectivity of the hydrogenation of said linear hydrocarbon diolefin to linear hydrocarbon olefin by adding to the hydrogenation mixture an aqueous solution of a zinc salt having a ratio of water/zinc of at least 1/1 by weight.

2. A process of hydrogenating a linear hydrocarbon diolefin according to claim 1, wherein the amount of said zinc salt is from 0.01 to 5% by weight of the linear diolefin.

3. A process of hydrogenating a linear hydrocarbon diolefin according to claim 1, wherein the hydrogenation is carried out at temperatures ranging from 20° to 60°C and at pressures between 1 and 50 atmospheres.

4. A process of hydrogenating a linear hydrocarbon diolefin according to claim 1, wherein the hydrogenation is carried out in the presence of an amine compound in the amount of not more than 0.5% by weight of the linear hydrocarbon diolefin.

5. A process of hydrogenating a linear hydrocarbon diolefin according to claim 4, wherein the amine compound is ammonia.

6. A process of hydrogenating a linear hydrocarbon diolefin according to claim 1, wherein the zinc salt is a member of the group consisting of zinc chloride, zinc sulfate, zinc nitrate, zinc acetate and zinc oxalate.

* * * * *

UNITED STATES PATENT AND TRADEMARK OFFICE
CERTIFICATE OF CORRECTION

PATENT NO. : 3,947,510
DATED : March 30, 1976
INVENTOR(S) : Morello Morelli and Fortunato DeMarco It is certified that error appears in the above-identified patent and that said Letters Patent are hereby corrected as shown below:

After line "[21] Appln. No. 382,055" insert

--[30]    Foreign Application Priority Data
          July 27, 1972 Italy.........27492/72--.

Column 1, line 15, Change "compound" to --compounds--.

line 49, After "complicated" insert --because--.

Column 2, line 27, After "ranges" insert --on--.

Signed and Sealed this

Fourth Day of March 1980

[SEAL]

Attest:

SIDNEY A. DIAMOND

Attesting Officer     Commissioner of Patents and Trademarks